United States Patent [19]

Apfel et al.

[11] Patent Number: 5,035,896
[45] Date of Patent: Jul. 30, 1991

[54] WATER INSOLUBLE DRUGS COATED BY COACERVATED FISH GELATIN

[75] Inventors: Marilyn A. Apfel, Bedminster; Isaac Ghebre-Sellassie, Stanhope; Russell U. Nesbitt, Somerville, all of N.J.

[73] Assignee: Warner-Lambert Company, Morris Plains, N.J.

[21] Appl. No.: 207,361

[22] Filed: Jun. 15, 1988

[51] Int. Cl.$^5$ .......................... A61K 9/50; A61K 9/64
[52] U.S. Cl. .................... 424/456; 424/490; 424/491; 424/492; 514/801; 514/774; 530/354; 530/857; 426/576
[58] Field of Search ............... 424/489, 490, 491, 492, 424/95, 456; 514/774, 801; 530/354, 857; 426/576

[56] References Cited

U.S. PATENT DOCUMENTS

| | | | |
|---|---|---|---|
| Re. 24,899 | 11/1960 | Green | 514/784 |
| 3,876,803 | 4/1975 | Stephan et al. | 426/656 |
| 3,984,391 | 10/1976 | Nitschmann et al. | 424/95 |
| 4,247,406 | 1/1981 | Widder et al. | 424/486 |
| 4,273,672 | 6/1981 | Vassiliades | 424/401 |

FOREIGN PATENT DOCUMENTS 1529055  6/1967  France ................................. 514/801

*Primary Examiner*—Douglas W. Robinson
*Assistant Examiner*—Jean C. Witz
*Attorney, Agent, or Firm*—Craig M. Bell

[57] ABSTRACT

According to this invention, the combination of a solid particulate water insoluble drug with a solid fish gelatin coating is produced by coacervation of the fish gelatin. The fish gelatin being soluble at ambient temperatures provides a basis for relatively low temperature coacervation impossible with other gelatins. Coacervation is brought about by the addition of conventional coacervation agents and the coacervating suspension containing gelatin and the agents is rendered insoluble by the addition of a suitable fixative such as glutaraldehyde.

9 Claims, No Drawings

WATER INSOLUBLE DRUGS COATED BY COACERVATED FISH GELATIN

BACKGROUND OF THE INVENTION

Many attempts have been made in the past to mask or eliminate noxious odors and tastes of drugs to enhance the dosage compliance of patients who are required to take these drugs. Coatings which have been used in the case of solid water insoluble particulates have all suffered from deficiencies of one sort or another relating either to processing difficulties and working with the coating materials themselves or from limited success in performing the masking function.

One method of dealing with drugs of this sort is to coat them in the form of microparticles. The coating of particles by coacervation is well known. U.S. Pat. No. 3,594,327 issued to Julius G. Beesey discloses a process for making minute capsules in which minute particles of water and misible material and hydrophillic film forming polymeric material such as gelatin are dispersed in water and coacervated so that the polymeric material deposits around each of the minute particles. The polymeric material is then rendered rigid and water insoluble by a suitable fixative such as copper sulfate. The concept of coacervation of gelatin around particulate matter is also described in U.S. Pat. No. 3,317,434 issued to Vels et al. and U.S. Pat. No. 3,176,001 also issued to Vels. This gelatin which is of the porcine bovine type, is also used to form gelatin capsules and for some granulations.

While coacervation of conventional bovine and porcine gelatin is known, commercial processes utilizing coacervation of bovine and porcine gelatin as a coating for water insoluble drug particles is essentially nonexistent. The reason for this is that the gelatin must be heated to approximately 40° C. before it is dissolved and ready for use. This temperature may adversely effect heat labile drugs and the increased temperature also makes the process difficult to work with.

Teleostean (fish) gelatin however is soluble in water at room temperature. This gelatin described for example in "Production of Glue and Gelatin from Fish" by J. C. Kernot and N. E. Speer, Department of Sol Ind. Research 2nd report of Adhesives Research Committee 1926, 23-33. Fish gelatin is also mentioned in U.S. Pat. No. 2,560,011 which teaches an extraction process for it. U.S. Pat. No. 3,873,749 issued to Carpenter et al. teaches a process for manufacturing a fish gelatin-alginate composition.

SUMMARY OF THE INVENTION

According to this invention, the combination of a solid particulate water insoluble drug with a solid fish gelatin coating is produced by coacervation of the fish gelatin. The fish gelatin being soluble at 5°-10° C. provides a basis for ambient temperature e.g. 16°-27° C. coacervation impossible with other gelatins. Coacervation is brought about by the addition of conventional coacervation agents and the coacervating suspension containing gelatin and the agents is rendered insoluble by the addition of a suitable fixative such as glutaraldehyde.

DETAILED DESCRIPTION OF THE INVENTION

This invention is directed to the coacervation of fish gelatin to form microparticles. These microparticles are particularly useful as a means for protecting particulate water insoluble drugs from exposure to oxygen or moisture and the barrier thus formed is also useful for masking of unpleasant taste and odor from such drugs. The process of this invention is particularly useful for drugs which are heat sensitive because of the low temperature water solubility of fish gelatin.

While all drugs which are water insoluble particulates may be used and benefit from the process of this invention, drugs as defined herein specifically exclude water insoluble particulate ion exchange resins such as cholystyramine. Cholystyramine, has thus far, proven resistant to coacervation. While not wishing to be bound by any theory it is postulated that the charge associated with the ion exchange resin is the reason for the difficulty in obtaining no satisfactory coacervation.

The process of this invention employs reagents useful for coacervation, either porcine or bovine gelatin. These reagents which are for example, lower alkyl alcohols such as ethanol, or short chained glycols, and inorganic salts such as sodium sulfate, when reacted with fish gelatin solutions coacervate the fish gelatin to provide particles which are insoluble in the modified aqueous solution. The subsequent addition of a fixative-cross linking agent such as glutaraldehyde renders the fish gelatin water insoluble. The insoluble particles can then be removed or collected from aqueous solution by conventional techniques such as ultracentrifugation, or filtration or the like. These harvested particles can be collected for conventional oral dosage forms.

Examples of the product of this invention follow. In all instances fish gelatin solution was obtained from Norlund Products Inc., New Brunswick, N.J. Fish gelatin contained 45% solids in solution.

EXAMPLE 1

A fish gelatin solution containing 6 grams of fish gelatin at a 45% solids ratio was diluted with 54 mls of water and was mixed together with 56 ml aliquot of 20% of sodium sulfate which, was added drop wise to the stirred solution over approximately 10 minutes.

After stirring for approximately, ½ hour 1 ml of 5% v/v glutaraldehyde was added. After 3½ minutes 60 mls of a 12% weight by weight solution of sodium metabisulfite was added to reduce the glutaradehyde to an alcohol to prevent further reaction.

The hardened soluble particles have a variety of size ranges with many below the 1 micron range. Particles below the micron range were not successfully harvested by filtration through a nylon 66 filter with a pore size of 0.45u. The filter was however useful in sorting the larger particles.

It should be noted that particles of all sizes were prepared with sodium sulfate and then successfully harvested by lyophilization. In addition, particles in the 100 nm range have been harvested by ultracentrifugation after first sorting the larger particles using centrifugation at lower speeds. It should further be noted that particles prepared by ultracentrifugation and lyophilization can be resuspended in water and do not form aggregates.

EXAMPLE 2

This example utilizes coacervation by ethanol. 12 grams of the 45% solid solution of fish gelatin was dissolved in 324 mls of distilled water. 500 mls of 95% ethanol was added drop wise with stirring over a period of approximately ½ hour, and the suspension was stirred for another ½ hour. Subsequently, 45 mls of 12.5% v/v of glutaraldehyde was added, and, after 20 minutes, 374 mls of a 12% w/w solution of sodium metabisulfite was added. The solution was filtered through a nylon filter, resuspended in a sodium dodecyl sulfate (SDS) solution, refiltered, and air dried to yield the gelatin particles with an approximate yield of 30%.

As was the case with Example 1 sodium metabisulfite solution was added to chemically reduce the remaining glutaraldehyde. The particle size distribution ranged generally from 0.1 microns to 5 microns.

The particles which had been subjected to the SDS treatment, were found to be easily dispersed in water without stirring and can be seen microscopically as individual spheres. The filter cake appears to contain SDS because upon the resuspension the weight of the new dry cake was reduced by 20%. A precipitate of barium dodecyl sulfate was formed when a solution of barium chloride was added to the filtrate. This cake is no longer dispersible in water. Preliminary experiments indicate that the particles thus formed are stable in 0.025% trypsin for several hours.

The use of SDS, of course, is not required when ethanol is used as the coacervating agent.

EXAMPLE 3

Coacervation of fish gelatin by sodium sulfite is performed around triamterine. Triamterine is a 6-phenyl-2, 4, 7-pteridinetriamine. It is a known diuretic. Three grams of 45% fish gelatin was dissolved in 27 ml of distilled water and 0.1 g of Tramterine was dispersed in the distilled water along with the fish gelatin. 28 ml 20% w/w sodium sulfate was added over approximately 20 minutes and the suspension was filtered another 30 minutes. 0.5 ml diluted with water to 5% v/v solution of glutaraldehyde was added and, after 3.5 minutes, 30 ml of sodium metabisulfite was added (12% w/w). The particles were filtered in a Whatman filter paper #541 and air dried. The particles appeared microscopically to be spheres of gelatin encircled drug and are quite distinct from the unencapsulated drug when subjected to a microscopic analysis. The filtered particles were air dried to a yellow aggregate weighing 0.25 g., which was not easily dispersed in water. However, upon lyophilization and subsequent resuspension in water, they appear as microscopically discrete particles. Population particle size mean is 9.5u and the range is between 2.5 and 50u.

The examples set forth above are currently preferred examples of producing coaverated fish gelatin. Particle size integrity and yield may be affected by several aspects of the production of particles such as the addition rate of coacervating agents, the stirring speed, the presence or absence of surfactant, the time allowed for the development of the coacervate, the glutaraldehyde fixation conditions, the cross linking agent itself (if another is substituted or combined with glutaraldehyde), the sodium dodecyl sulfate wash concentration and the harvesting process. Obviously the particular choice of components, particle size, the presence of SDS or similar compounds will vary with the particular choice of drugs and the desired release rate. These variables are well within the skill of the art once the broad concept of this invention is set forth, namely the concept of coacervation of fish gelatin and the use of the coaverate as a protective coating for drug particles.

We claim:

1. A composition comprising a solid particulate water insoluble drug which is microencapsulated with a gelatin solution by coacervation and fixation at ambient temperature wherein the gelatin is fish gelatin.

2. The combination of claim 1 wherein the fish gelatin includes a coacervating agent.

3. The combination of claim 1 wherein the coacervating agent is selected from the group consisting of edible sulfates and edible alcohols.

4. The composition of claims 1, 2 or 3 wherein the gelatin solution is rendered water insoluble about the particulate drug by a fixative.

5. The composition of claims 1, 2 3 or 4 wherein glutaraldehyde is added to the gelatin solution as a fixative.

6. A process for the production of the composition of claim 1 comprising:
   (a) slowly adding a coacervating agent to an aqueous solution of fish gelatin and the particulate water insoluble drug at ambient temperature until the gelatin forms a suspension; and
   (b) contacting the suspension with a fixative to form individual particles of water insoluble fish gelatin about said drug.

7. The process of claim 6 wherein the coacervating agent is selected from the group consisting of edible sulfates and alcohols.

8. The process of claim 6 or 7 wherein the fixative is glutaraldehyde.

9. The process of claim 6 wherein the particulate water insoluble drug is suspended in the aqueous solution prior to the addition of the coacervating agent.

* * * * *